US00PP25907P3

(12) United States Plant Patent

Kobayashi et al.

(10) Patent No.: US PP25,907 P3

(45) Date of Patent: Sep. 15, 2015

(54) *TRIFOLIUM* PLANT NAME 'TFLRE04-0'

(50) Latin Name: *Trifolium repens*
Varietal Denomination: TFLRE04-0

(71) Applicants: Takayuki Kobayashi, Fukaya (JP); Kuzunori Sato, Tokyo (JP)

(72) Inventors: Takayuki Kobayashi, Fukaya (JP); Kuzunori Sato, Tokyo (JP)

( * ) Notice: Subject to any disclaimer, the term of this patent is extended or adjusted under 35 U.S.C. 154(b) by 76 days.

(21) Appl. No.: 13/998,991

(22) Filed: Dec. 30, 2013

(65) Prior Publication Data

US 2015/0189820 P1 Jul. 2, 2015

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para

(74) *Attorney, Agent, or Firm* — Cassandra Bright

(57) ABSTRACT

A new and distinct *Trifolium* cultivar named 'TFLRE04-0' is disclosed, characterized by Unique deep red color, compact size, small leaf size and a 4 leaflet occurring rate of more than 40% of the plant. The new variety is a *Trifolium,* typically produced as an ornamental plant.

1 Drawing Sheet

Latin name of the genus and species: *Trifolium repens.*
Variety denomination: 'TFLRE04-0'.

BACKGROUND OF THE INVENTION

The new cultivar is a product of a planned breeding program. The objectives of the planned breeding program were to develop new *Trifolium* varieties with interesting foliage for ornamental purposes. The breeding program was developed under the direction of the co-inventors, Takayuki Kobayashi and Kazunori Sato, in Japan. The new variety originated from a cross pollination of the seed parent, an unpatented, unnamed, proprietary variety of *Trifolium repens* and the pollen parent, a different unpatented, unnamed, proprietary variety of *Trifolium repens*. The crossing was made during 2007.

The new variety was selected by the inventors, Takayuki Kobayashi and Kazunori Sato, in September 2011 in a group of seedlings resulting from the crossing. The new cultivar was selected in a non-commercial greenhouse in Japan.

Asexual reproduction of the new cultivar 'TFLRE04-0' was first performed at a non-commercial greenhouse in Japan by vegetative cuttings in March 2012. More than 5 generations have been reproduced by vegetative cuttings. Subsequently, propagation has also been performed by tissue culture. Both methods have shown that the unique features of this cultivar are stable and reproduced true to type.

SUMMARY OF THE INVENTION

The cultivar 'TFLRE04-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TFLRE04-0'. These characteristics in combination distinguish 'TFLRE04-0' as a new and distinct *Trifolium* cultivar:

1. Unique foliage with red color and typically 3, 4 or 5 leaflets per leaf.

2. Typically, at least 40% of foliage has 4 leaflets per leaf.
3. Leaf size is little smaller than typical *Trifolium* foliage.
4. During winter time foliage is very deep red color, much darker than the summer color.
5. Plant size is compact.

PARENT COMPARISON

Plants of the new cultivar 'TFLRE04-0' are similar to the proprietary *Trifolium repens* seed parent in most horticultural characteristics. The new variety however differs in the following characteristics:

1. Different foliage coloration.
2. Different leaflet quantity per leaf.
3. Faster growth rate.

Plants of the new cultivar 'TFLRE04-0' are similar to the proprietary pollen parent in most horticultural characteristics. The new variety however differs in the following characteristics:

1. Different foliage coloration.
2. Different leaflet quantity per leaf.
3. More vigorous plant.

COMMERCIAL COMPARISON

'TFLRE04-0' can be compared to the unpatented commercial variety *Trifolium* 'Just Wish Happy Life'. Plants of 'Just Wish Happy Life' are similar to plants of 'TFLRE04-0' in most horticultural characteristics. However 'TFLRE04-0' differs from 'Just Wish Happy Life' in the following characteristics:

1. Faster growth rate.
2. Different leaflet shape.
3. Autumn and winter color is more intense.

BRIEF DESCRIPTION OF THE PHOTOGRAPH

The accompanying photograph in FIG. 1 illustrates in full color a typical plant of 'TFLRE04-0' grown in a greenhouse in Santa Paula, Calif.

This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TFLRE04-0' plants grown in a climate controlled greenhouse in Santa Paula, Calif. Temperatures ranged from 20° C. to 25° C. at night to 25° C. to 32° C. during the day. No artificial light, photoperiodic treatments were given to the plants. Plants were grown in 50% shade. Measurements and numerical values represent averages of typical plant types. Botanical classification: *Trifolium repens* 'TFLRE04-0'.

PROPAGATION

Root description: Fine, non-fleshy roots. Roots approximately 0.3 cm thick, colored near RHS White 155A.

PLANT

Growth habit: Herbaceous, upright perennial with basally emerging foliage. Foliage emerges from a system of above ground rhizotamous stems.
Plant shape: Upright, petioles slightly arching out and undulating.
Height: Approximately 15 cm to top of foliar plane.
Plant spread: Approximately 38 cm in a 6 inch pot.
Pot size of plant described: 8 inch.
Growth rate: Rapid and vigorous.
Branching characteristics: No true branching. Leaves emerge direct from above ground rhizotamous stems.
Rhizotamous stems: Approximately 5 to 7 main stems on a plant of 6 months.
- *Diameter*.—Approximately 0.3 cm.
- *Length*.—Variable, average range 3 to 20 cm. Stems will circle the edge of the pot. Frequent rooting from these stems.
- *Color*.—Near Yellow-Green 144D.
- *Texture*.—Smooth.
- *Appearance*.—Shiny.

Age of plant described: Approximately 6 months.

FOLIAGE

Leaf:
- *Number of leaves per plant*.—Approximately 80 to 100 compound leaves.
- *Arrangement*.—Compound leaf made up of 3 to 5 leaflets. Leaflets rotate, if 3 to 5 occurring. Opposite arrangement when 4 leaflets. 4 leaflet arrangement is most common.

Compound leaf:
- *Average diameter*.—4.5 cm.
- *Average depth*.—1.3 cm.

Leaflets:
- *Average length*.—1.8 to 2.5 cm, including leaflet petiole.
- *Average width*.—1.2 to 2.0 cm.
- *Shape of blade*.—Orbicular.
- *Aspect*.—Slightly undulating, upward fold from mid vein.
- *Apex*.—Rounded.
- *Base*.—Rounded.
- *Margin*.—Very fine serration.
- *Attachment*.—Stalked.
- *Appearance*.—Matte, both upper and lower surfaces.
- *Texture of top surface*.—Smooth.
- *Texture of bottom surface*.—Smooth.
- *Color*.—Young foliage upper side: Near RHS Greyed-Purple N186C, margin Yellow-Green 147A, but darker. Young foliage under side: Near RHS Greyed-Purple 183A, margin Yellow-Green 147A. Mature foliage upper side: Near RHS Greyed-Purple N186C, very thin margin Yellow-Green 147A, but darker. Mature foliage under side: Near RHS Greyed-Purple 187A, margin Yellow-Green 147A.

Leaflet petiole:
- Length.—Approximately 0.15 cm.
- *Width*.—Approximately 0.1 cm.
- *Color*.—Near Yellow-Green 144C.
- *Texture*.—Smooth.

Venation:
- *Type*.—Pinnate.
- *Venation coloration upper side*.—Near RHS Greyed-Purple N186C.
- *Venation coloration under side*.—Near RHS Yellow-Green 144B.

Leaf petiole:
- *Length*.—Approximate range from 6.5 cm to 16 cm.
- *Width*.—Approximately 0.3 cm.
- *Color*.—Near Green 143C.
- *Texture*.—Smooth.
- *Appearance*.—Shiny.
- *Strength*.—Highly flexible, moderately strong.

INFLORESCENCE

Flowering has not been observed to date.

OTHER CHARACTERISTICS

Disease resistance: Neither resistance nor susceptibility to the normal diseases and pests of *Trifolium* observed to date.
Drought tolerance and cold tolerance: The new cultivar is a typical *Trifolium*, cold tolerant to approximately 5° to 7° C. and does not tolerate drought.
Fruit/seed production: Not observed.

What is claimed is:

1. A new and distinct cultivar of *Trifolium* plant named 'TFLRE04-0' as herein illustrated and described.

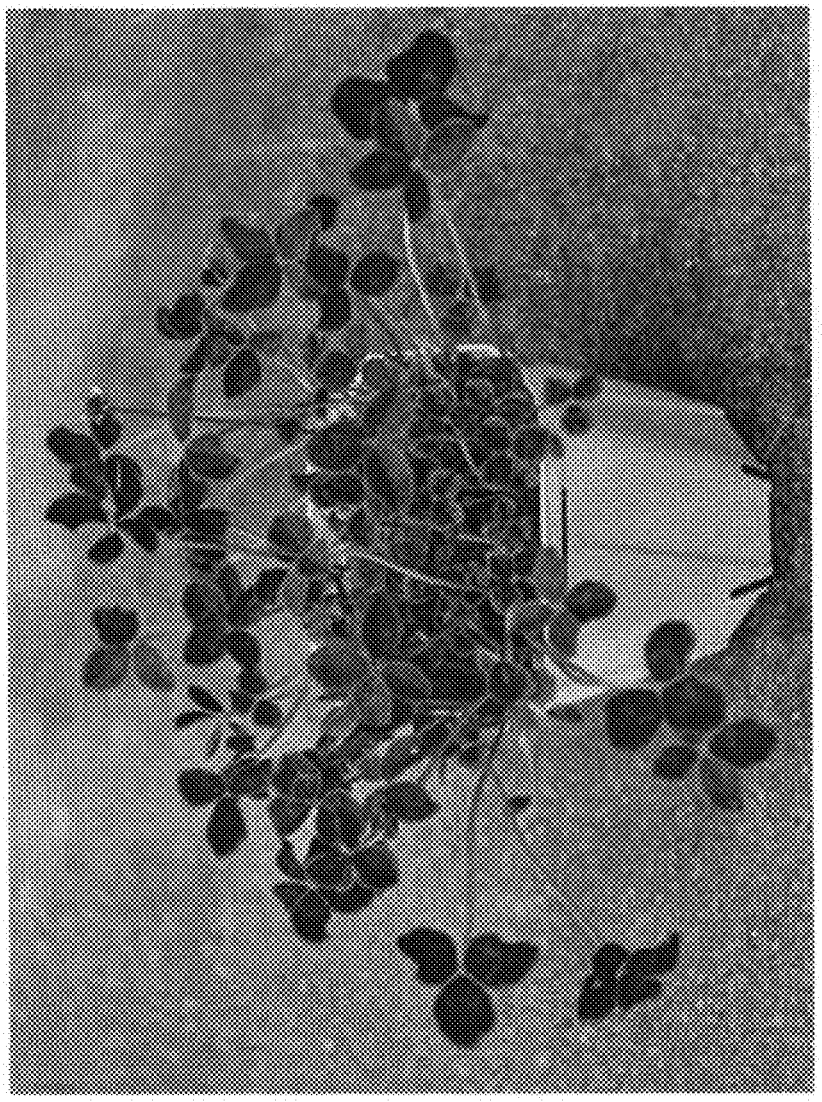

* * * * *